United States Patent [19]

Draenert

[11] Patent Number: 5,554,190
[45] Date of Patent: Sep. 10, 1996

[54] PROSTHESIS COMPONENT AND A METHOD OF PRODUCING IT

[76] Inventor: Klaus Draenert, Gabriel-Max-Str. 3, D-8000 München 80, Germany

[21] Appl. No.: 325,350

[22] PCT Filed: Apr. 26, 1993

[86] PCT No.: PCT/EP93/01002

§ 371 Date: Oct. 21, 1994

§ 102(e) Date: Oct. 21, 1994

[87] PCT Pub. No.: WO93/21863

PCT Pub. Date: Nov. 11, 1993

[30] Foreign Application Priority Data

Apr. 24, 1992 [DE] Germany ............... 42 13 599.0

[51] Int. Cl.$^6$ ..................................................... A61F 2/28
[52] U.S. Cl. .................. 623/16; 623/22; 623/901; 378/57; 364/413.19; 364/474.24
[58] Field of Search ................. 623/16, 901, 22; 378/18, 57, 56, 207; 364/474.24, 413.14, 413.15, 413.16, 413.19, 468

[56] References Cited

U.S. PATENT DOCUMENTS

| 3,893,196 | 7/1975 | Hochman | 3/1.91 |
| 4,436,684 | 3/1984 | White | 264/138 |
| 4,873,707 | 10/1989 | Robertson | 378/18 |
| 4,936,862 | 6/1990 | Walker et al. | 623/23 |
| 5,150,304 | 9/1992 | Berchem et al. | 364/474.24 |
| 5,274,565 | 12/1993 | Reuben | 364/474.24 |

FOREIGN PATENT DOCUMENTS

| 0093869A1 | 11/1983 | European Pat. Off. . |
| 0255797A1 | 2/1988 | European Pat. Off. . |
| 0257222A1 | 3/1988 | European Pat. Off. . |
| 0425714A1 | 5/1991 | European Pat. Off. . |
| 0479257A1 | 4/1992 | European Pat. Off. . |
| WO89/10730 | 11/1989 | WIPO . |
| WO90/02533 | 3/1990 | WIPO . |

OTHER PUBLICATIONS

Fertigung von Knochenmodellen nach Computer–Tomographie–Daten zur verwendung in Chriurgie and Orthopadie.

*Primary Examiner*—Michael J. Milano
*Attorney, Agent, or Firm*—Kinney & Lange, P.A.

[57] ABSTRACT

The present invention relates to a prosthesis component for anchoring with or without using bone cement and to a method of producing it. The prosthesis component, which can be produced by CAD and image-analysis methods, provides for the largest possible surface for the transmission of forces, and its mass and rigidity can be adapted to the individual properties of the bone.

18 Claims, 1 Drawing Sheet

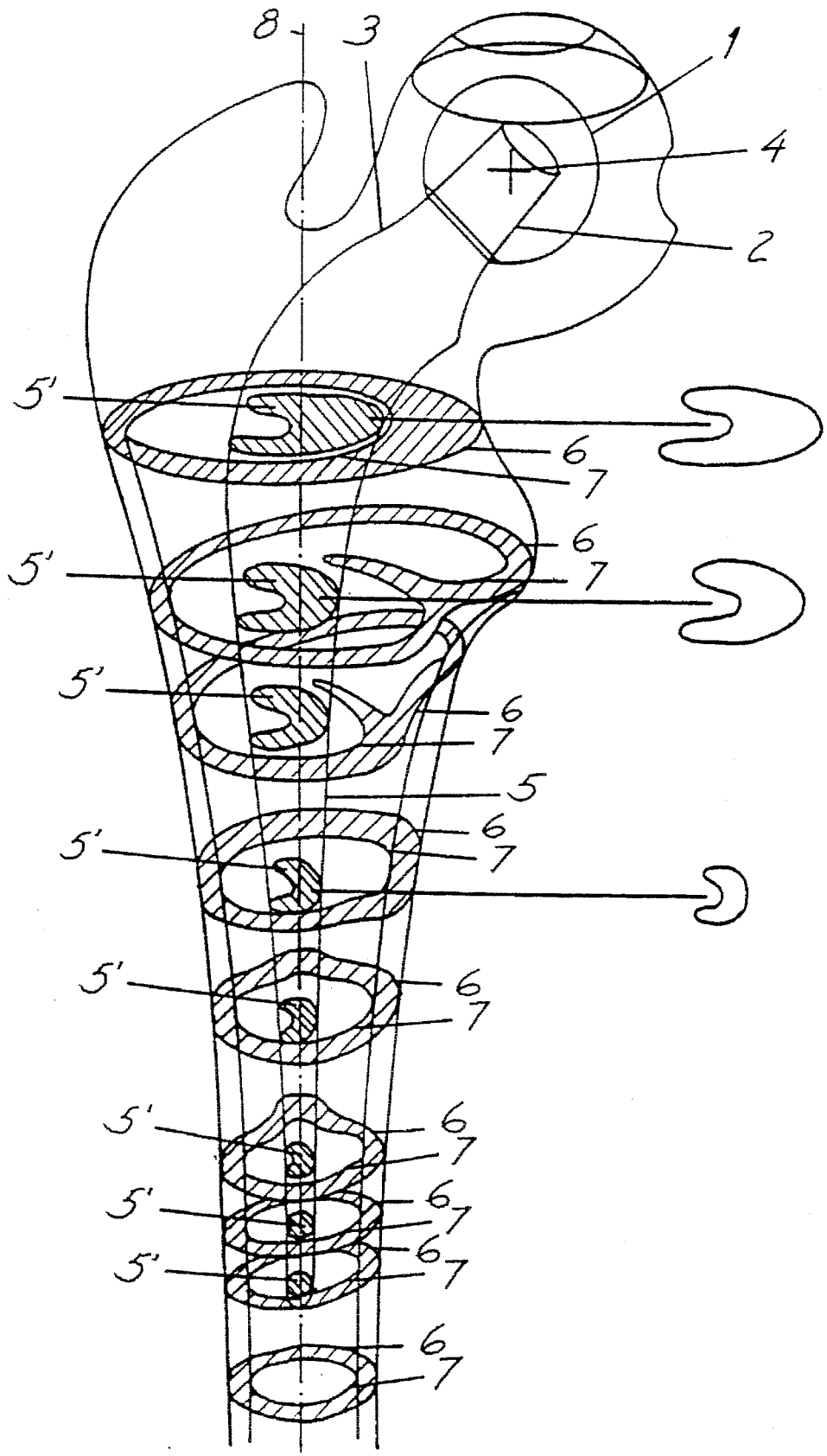

PROSTHESIS COMPONENT AND A METHOD OF PRODUCING IT

BACKGROUND OF THE INVENTION

The present invention relates to a prosthesis component for anchoring with or without using bone cement and a method of producing it.

In the fields of surgery and orthopaedics with respect to the locomotor system, the artificial joint replacement has become a standard surgical intervention and is today one of the most frequently carried out operations of all. The long-term results of replaced joints have been quite variable and the life time of, for example, replaced hip joints ranges from few weeks up to 27 years (Draenert and Draenert 1992).

It has been found out by scientific research that different factors are responsible for the loosening of an endoprosthesis component, such as infections, insufficient surgical skills, choice of the wrong implant and excessive strain. Nevertheless, so far many cases of loosening could not be explained in a satisfying manner. It has only been detected that certain combinations of factors frequently lead to a loosening, such as a massive cement-free implant used in combination with the bone of a rheumatic. Such types of prostheses which were to interlock within the bone and were implanted together with bone cement showed (Draenert 1988) that bone cement as a filling material between metal and bone cannot fulfil an anchoring function but is pulverised.

The problem involved in the anchoring of prosthesis components could in the end be attributed to the phenomenon of bone deformability. This explained why an easily deformable bone of a rheumatic is deformed by a metal prosthesis anchored without cement such that rapid loosening ensued. On the other hand, it could be shown that a fragile or soft spongiosa as well as a normal spongiosa (cancellous bones) can be stiffened by means of polymethylmethacrylate (PMMA) bone cement and thus gets extremely rigid (Draenert and Draenert 1992). A thus stiffened bone structure could be found with all those implants which had successfully been used for 10 to 20 years and could be histologically examined. On the other hand, quite compact femora could be provided with prosthesis components without using bone cement as an anchoring means, and several of these prosthesis components have successfully been implanted for about 10 years (Draenert and Draenert 1992). However, in these cases, the results could not be reproduced either.

It is an object of the present invention to provide a prosthesis component which can be anchored with or without using bone cement and with which, after its implantation, good long-term results can be expected.

This object is achieved by the present invention.

BRIEF DESCRIPTION OF THE DRAWING

The Figure depicts a front view of the (implanted) prosthesis.

DESCRIPTION OF THE PREFERRED EMBODIMENT(S)

In connection with the invention, the problem has been investigated how the strength of a bone influences the life time of an implant. By means of histological studies it could clearly be proven that soft, deformable bones only show a stable anchoring if the implants used have a low mass.

The present invention is based on the following findings regarding the anchoring of prostheses: Every bone exhibits an individual shape and an individual strength; therefore, both factors must be taken into account when selecting the prosthesis. A solid, compact bone is a good indication for metal-bone anchoring without using bone cement. Two factors are above all important in this context: 1. to obtain the best possible primary stability of the anchorage and 2. to provide the largest possible surface for the transmission of forces between the prosthesis and the bone. It has, however, to be considered that the various compartments of the bone, such as epiphysis, metaphysis and diaphysis, have completely different shapes and strengths. When implanting the prosthesis component using bone cement, the shape of the bony bed, for example the medullary cavity, has also to be taken into account since an incomplete cement sheath results in its premature destruction. There were early trials to adapt the prosthesis shaft to the medullary cavity, cf. EP-A-0 038 908; however, it was rapidly found out that one single implant design could not be adjusted to the variety of different bone shades (Noble et al., 1988); moreover, there was no possibility of determining the strengths of a bone and considering them when designing a prosthesis.

In connection with the invention, the problem has been investigated how the strength of a bone influences the life time of an implant. By means of histological studies it could clearly be proven that soft, deformable bones only show a stable anchoring if the implants used have a low mass.

In connection with the present invention, it has been found out that there is a good correlation between the density of a bone and its strength. According to the invention, the density of a bone can therefore be used as a measure for its strength. By combining various image-analysing and computer-aided calculations, a method could be found with which the morphology of the bony bed as well as the strength of the bone could be determined and taken into account for the design of a prosthesis component. These experiments resulted in a design of a prosthesis component which can be fit ideally into the bony bed and whose mass and/or stiffness can be selectively changed such that in each case the largest possible surface is provided for the transmission of force between prosthesis and bone.

The mass and/or the stiffness of the prosthesis component according to the present invention can be adjusted to the individual properties of the bone. In case of a femoral prosthesis component, for example in the medial, in particular the medioproximal portion of the prosthesis, the bending strength of the prosthesis is the decisive factor. In the lateral portion of the prosthesis, tensile stresses are predominant in the distal as well as in the proximal portion so that there the tensile strength of the prosthesis is also of importance. In the distal portion, the tensile strength is of particular importance. Due to the muscular attachments not covering the neck of the femur and the head of the neck of the femur there are also torsional forces. In case of other prosthesis components, such as shoulder, elbow, knee, hand, finger and ankle joint components, the desired material properties also vary in the different portions of prosthesis components. In the present invention, the aforementioned material properties are mostly summarised as "rigidity". According to the present invention, the rigidity of the prosthesis and/or its mass is adapted to the individual properties of the bone.

There are several ways of adaptation; for example, the material of the prosthesis can be selected according to the individual properties of the bone. In case of a dense bone, a material having a higher specific mass and a higher rigidity can be selected whereas in case of a bone with a low density, the material to be selected has a low specific mass and rigidity. CoCrMo alloys, Ti, Ti alloys, steel, plastics or composite materials can for example be used as materials of the prosthesis.

It is also possible to select an inhomogeneous material for the prosthesis component, in the sense that in portions of higher bone density a material of higher specific mass and/or rigidity is used than in portions of lower bone density. In this connection, it has to be considered that the bone density can greatly vary, and that, e.g., in the femur the density of the spongy portion of the bone can be merely 15 to 20% of that of the compact substance of the bone. When using a porous prosthesis material, the desired inhomogeneity of the material can for example be obtained by varying the pore size and reducing it in portions of higher bone density. Composite materials can also be used as material for the prosthesis component wherein, for example, the fibre content of the composite material can vary along the axial length of the prosthesis component. Thus, in particular the rigidity of the prosthesis component can be varied and adapted to the bone density.

Furthermore, the mass and/or the rigidity of the prosthesis component can be adapted to the individual properties of the bone by a suitable selection of the shape of the prosthesis component, particularly of the cross-section of the prosthesis component in various bone portions. If, for example, at least an essential part of the length of the femoral prosthesis component is U-shaped or horseshoe-shaped in its cross-section, as proposed in WO 90/02533 which corresponds to U.S. application Ser. No. 07/466,326 and is hereby incorporated by reference, the cross-sectional area and thus the prosthesis mass can be adapted in various sections by a suitable selection of the size and depth of the groove or the slot between the two arms of the U-shaped cross-section. A transition from a solid shaft to a U-shaped cross-section with very thin arms is conceivable according to the invention. The largest possible surface for the transmission of forces between the bone and the prosthesis is guaranteed by the fact that the prosthesis component forms an uninterrupted surface or closed contour in its medial, dorsomedial and anteromedial portions.

The mass and/or the rigidity can for example also be changed, in particular in order to reduce the mass and/or rigidity, by providing bore holes which partly pass through the prosthesis shaft, such as blind holes, or bore holes which completely pass through the prosthesis shaft. On the other hand, ridges and/or reinforcing elements provided at the outer and/or inner contours of the prosthesis, for example of a U-shaped prosthesis shaft, can increase the mass and/or rigidity of the prosthesis component. Such elements can be provided either on portions or over essentially the whole length of the prosthesis component.

The mass and/or the rigidity of the prosthesis component is adapted to the bone density preferably by a linear correlation between the bone density and the mass and/or rigidity of the prosthesis component; that means, for example, that the mass or rigidity of the prosthesis in the respective portion of the prosthesis component is increased proportionally if the bone density is doubled.

In detail, it can be proceeded as follows in order to design and produce such an individual prosthesis component:

A patient having a deformed joint changed due to arthrosis is examined to obtain a series of bone sections. Said examination can be made either by a CT scanner or by nuclear spin tomography or by means of histological sections. Subsequently, stacked images of the individual section are provided, and stacked images of the joint are digitized and stored as cross-sectional images. So-called binary images are produced of the cross-sectional images by means of image analytical methods, i.e. black and white contrast images whose inner and outer contours can be analysed. The inner contour is put together in a 3D model. The axis or the axes of the joint are determined and depicted together with the contour model with the articular surfaces by means of the image analysis (cf. the Figure which depicts a femoral prosthesis component as an example).

The shape of the shaft of the prosthesis component can subsequently be adapted to the shape of the bony bed. By means of several, preferably six to ten sections which are evenly distributed along the length of the bone, the density per unit area of the bone is determined via the binary image and compared with the corresponding section of a normal bone which has been previously analysed. This comparison results in a correlation factor as a measure of the strength of the individual bone. If the specific bone density corresponds to that of the normal bone, the contour model of the bony bed is eccentrically and/or concentrically reduced by 20 to 50% in case of cemented components and by 1 to 20%, preferably 5 to 10%, in case of cement-free components in order to determine the cross-section of the prosthesis component in the respective section. If the specific bone density is lower than that of the normal bone, the contour model is correspondingly more reduced to determine the cross-section of the prosthesis. The values between the individual sections can be interpolated. In case of a prosthesis component which is to be anchored with bone cement, the prosthesis cross-section is preferably determined such that the thickness of the bone cement sheath surrounding the prosthesis is inversely proportional to the respective bone density. The set of data of the contour model is transferred together with the position of the centre of rotation or the joint axis to a CAD unit. In the CAD unit, the axis of the contour model is determined and undercuts in the design are corrected such that the prosthesis component can be inserted within the bone cement, if bone cement is used, with a rectilinear movement and/or with a slight screwing movement without contacting the bone. The design such obtained is re-transferred to the image-analysis unit in which a double contour model of the outer and the inner contours of the bone is produced, into which the prosthesis component can be fitted. Finally, while considering and correcting the enlargement ratio, the prosthesis component is projected into the ap X-ray image (path of the rays anterior-posterior) and the axial X-ray image and inserted along its implantation axis. The mass and/or rigidity of the prosthesis is determined to be proportional to the bone density. Then the CAD data set is completed with the standard constructional data of the prosthesis and of the implantation instrumentarium and transferred to a milling unit. In the milling unit, the prosthesis component is milled from a blank, which is for example made of $V_4A$ steel. Upon a surface treatment, the prosthesis component is washed and sterilised and can then be inserted.

In the following, the present invention is explained in more detail by means of the attached Figure. The Figure shows as an example of an embodiment of the prosthesis component according to the invention a cement-free femoral prosthesis component; cross-sections of the prosthesis as well as the inner and outer contour models of the femur are depicted in different sectional planes for further explanation.

The prosthesis according to the Figure, which is schematically depicted in the femur, comprises an attachable spherical head 1 which sits on a cone 2 of the neck portion 3 of the prosthesis. Reference sign 4 designates the centre of rotation. The neck portion 3 is fixedly connected to a shaft 5 of the prosthesis. In the sectional planes which are approximately evenly distributed over the length of the proximal femur and in which the bone density per unit area is determined, the optimum shaft cross-sections 5' obtained as described above are drawn. Eight hatched shaft cross-sections 5' are drawn into the Figure and, for further clarification, three shaft cross-sections are additionally drawn at the side of the femur. Preferably, the bone density and the optimum shaft cross-section ensuing therefrom are determined in six to ten, for example nine sectional planes. Reference sign 6 designates the outer contour model and reference sign 7 the inner contour model of the femur in each of the sectional planes which are obtained by the image analysis. The mass and/or rigidity of the prosthesis in the individual sectional planes can be adjusted by designing the shaft cross-sections suitably. If, for example, the mass is to be low, the slot or recess in the U-shaped shaft cross-section is enlarged, wherein at the same time the largest possible surface for the transmission of forces between prosthesis and bone is provided in the medial portion of the prosthesis. If the specific mass in a sectional plane is changed, the rigidity of the prosthesis component in this portion also changes, as a rule. Reference sign 8 designates the constructional axis of the prosthesis which is at the same time the axis of the medullary canal and the implantation axis.

Literature:

Draenert K. (1988), Forschung und Fortbildung in der Chirurgie des Bewegungsapparates 2, zur Praxis der Zementverankerung, Munich, Art and Science.

Draenert K. and Draenert Y. (1992), Forschung und Fortbildung in der Chirurgie des Bewegungsapparates 3, die Adaptation des Knochens an die Deformation durch Implantate, Munich, Art and Science.

Noble P. C., Alexander J. W., Lindahl L. J., Yew D. T., Granberry W. M., Tullos H. S., Clinical Orthopaedics and Related Research, No. 235, October 1988, pp 148–163.

I claim:

1. A method of producing a prosthesis component for anchoring with using bone cement and also for anchoring without using bone cement, in a bony bed in the epiphyseal, metaphyseal or diaphyseal portion of a bone, the bone having outer and inner contours, the prosthesis component produced thereby providing a surface for transmission of forces between the bone and the prosthesis component, the prosthesis component having a mass and a rigidity, the method comprising the following steps:

three-dimensionally reconstructing the bony bed from a series of sections of the bone;

producing a contour model of the bone including the outer and inner contours;

determining mean density of the bone in individual bone sections; and adapting the prosthesis component to the bony bed by determining a material property of the prosthesis component to correlate with the mean density in the individual bone sections.

2. The method according to claim 1, wherein the prosthesis component is adapted such that the material property is proportional to the mean density of the individual bone sections.

3. The method according to claim 1, wherein the sections are sections obtained by a method selected from the group consisting of: CT scan, nuclear spin tomography, and histology.

4. The method according to claim 1, wherein, in the reconstruction of the bony bed, stacked images of individual sections are digitized and electronically stored subsequently processed to the contour model.

5. The method according to claim 1, wherein the prosthesis component comprises a shaft, and wherein a shape of the shaft is adapted to the contour model.

6. The method according to claim 1, wherein a ratio between a cross-section of the prosthesis component and a cross-section of the bony bed is determined in each individual bone section to correlate to the mean density per unit area determined in the individual bone section.

7. The method according to claim 6, wherein the bone density per unit area, compared with a specific density per unit area of a corresponding normal bone, results in a factor which is used as correlation factor for the determination of the ratio between the cross-section of the prosthesis component and the cross-section of the bony bed.

8. The method according to claim 7, wherein the prosthesis component is for use with cement, and wherein the cross-section of the inner contour of the contour model is reduced by 20 to 50% according to the correlation factor to determine the cross-section of the prosthesis component.

9. The method according to claim 1, wherein an area of a cross-section of the prosthesis component is between 30 and 90% of an area of a corresponding cross-section of the bony bed.

10. The method according to claim 1, wherein the prosthesis component is for use with cement, wherein cross-sectional circumference of the prosthesis component is constantly 60 to 80% of cross-sectional circumference of the inner contour of the bony bed.

11. The method according to claim 1, wherein the prosthesis component is implanted with bone cement in a cement sheath, wherein a cross-section of the prosthesis component is determined from the mean density of individual bone sections such that thickness of the cement sheath is approximately inversely proportional to the mean density of the individual bone sections.

12. The method according to claim 1, wherein data of the contour model of the prosthesis component are transmitted to a computer design system and processed such that the prosthesis component can be implanted along an implantation axis.

13. The method according to claim 1, wherein the material of the prosthesis component is selected from a group consisting of: CoCrMo alloy, titanium, titanium ally, steel, plastics, and composite material.

14. The method according to claim 1, wherein the material property is mass of the prosthesis component.

15. The method according to claim 1, wherein the material property is rigidity of the prosthesis component.

16. The method according to claim 7, wherein the prosthesis component is for cement-free use, and wherein the cross-section of the inner contour of the contour model is reduced by 1 to 20% according to the correlation factor to determine the cross-section of the prosthesis component.

17. The method according to claim 1, wherein the prosthesis component is for cement-free use, wherein cross-sectional circumference of the prosthesis component is constantly 70 to 95% of cross-sectional circumference of the inner contour of the bony bed.

18. A prosthesis component produced by the method comprising the following steps:

three-dimensionally reconstructing a bed from a series of section of a bone;

producing a contour model of the bone including the outer and inner contours;

determining mean density of the bone in individual bone sections; and adapting the prosthesis component to the bony bed by determining a material property of the prosthesis component to the bony bed by determining a material property of the prosthesis component to correlate with the mean density in the individual bone sections.

* * * * *

UNITED STATES PATENT AND TRADEMARK OFFICE
CERTIFICATE OF CORRECTION

PATENT NO. : 5,554,190
DATED : SEPTEMBER 10, 1996
INVENTOR(S) : KLAUS DRAENERT

It is certified that error appears in the above-indentified patent and that said Letters Patent is hereby corrected as shown below:

Col. 2, line 55, after "femur", insert --,--

Col. 6, line 54, before "bed", insert --bony--

Col. 6, line 55, delete "section", insert --sections--

Signed and Sealed this

Twenty-first Day of January, 1997

Attest:

BRUCE LEHMAN

*Attesting Officer*   *Commissioner of Patents and Trademarks*